(12) United States Patent
Gheorghiu et al.

(10) Patent No.: US 11,733,323 B2
(45) Date of Patent: Aug. 22, 2023

(54) SYSTEMS AND METHODS FOR MEASURING CELLULAR RESPONSE TO TARGET ANALYTES BY CONTROLLED APPLICATION OF AN OSCILLATING STIMULUS

(71) Applicant: Centrul International de Biodinamica, Bucharest (RO)

(72) Inventors: Eugen Gheorghiu, Bucharest (RO); Mihai S. David, Bucharest (RO); Mihaela Gheorghiu, Bucharest (RO)

(73) Assignee: Centrul International de Biodinamica, Bucharest (RO)

( * ) Notice: Subject to any disclaimer, the term of this patent is extended or adjusted under 35 U.S.C. 154(b) by 1106 days.

(21) Appl. No.: 16/438,866

(22) Filed: Jun. 12, 2019

(65) Prior Publication Data
US 2019/0383888 A1    Dec. 19, 2019

(51) Int. Cl.
*G01R 33/09* (2006.01)
*G01R 33/00* (2006.01)
*G01N 33/52* (2006.01)
*G01N 33/543* (2006.01)

(52) U.S. Cl.
CPC ......... *G01R 33/091* (2013.01); *G01N 33/526* (2013.01); *G01N 33/528* (2013.01); *G01N 33/54333* (2013.01); *G01R 33/0094* (2013.01)

(58) Field of Classification Search
CPC .............. G01R 33/091; G01R 33/0094; G01N 33/526; G01N 33/528; G01N 33/54333; G01N 27/745; G01N 33/5008; G01N 33/5438; G01N 33/54326
See application file for complete search history.

(56) References Cited

U.S. PATENT DOCUMENTS

| 5,187,096 A | 2/1993 | Giaever et al. |
| 6,280,586 B1 | 8/2001 | Wolf et al. |
| 6,377,057 B1 | 4/2002 | Borkholder |
| 9,315,855 B2 * | 4/2016 | Gheorghiu ......... G01N 21/1717 |

(Continued)

FOREIGN PATENT DOCUMENTS

| EP | 2631652 A1 | 8/2013 |
| WO | 2005077104 A | 8/2005 |
| WO | 2017192579 A | 11/2017 |

OTHER PUBLICATIONS

Banerjee et al., "Mammalian cell-based biosensors for pathogens and toxins", Trends in Biotechnology, vol. 27, No. 3, pp. 179-188, Mar. 2009.

(Continued)

*Primary Examiner* — Dharti H Patel
(74) *Attorney, Agent, or Firm* — Law Office of Andrei D Popovici, PC

(57) ABSTRACT

Described systems and methods allow the detection and quantitative estimation of changes in the properties of a liquid sample comprising living biological cells, the changes caused by exposure to a target analyte such as a toxin, drug, pesticide, etc. A variable stimulus such as an oscillating magnetic field is applied to the sample, inducing variations in a position or shape of a constituent of the sample. Such variations produce measurable variations in electric and/or optical properties of a sensor, variations which allow a precise quantification of changes due to exposure to the target analyte.

18 Claims, 6 Drawing Sheets

(56) References Cited

U.S. PATENT DOCUMENTS

| | | |
|---|---|---|
| 9,612,234 B2 | 4/2017 | Li et al. |
| 11,630,069 B2* | 4/2023 | Kemp .................. A61B 5/412 422/69 |
| 2016/0178628 A1 | 6/2016 | Abdolahad et al. |
| 2019/0383888 A1* | 12/2019 | Gheorghiu ....... G01N 33/54333 |

OTHER PUBLICATIONS

Behm et al., "Cytotoxic Potency of Mycotoxins in Cultures of V79 Lung Fibroblast Cells", Journal of Toxicology and Environmental Health, Part A: Current Issues, vol. 75, Issue 19-20, pp. 1226-1231, published online Sep. 20, 2012.

Ceriotii et al., "Assessment of cytotoxicity by impedance spectroscopy", Biosensors and Bioelectronics, vol. 22, Issue 12, pp. 3057-3063, Jun. 15, 2007.

Gheorghiu et al., "Label free sensing platform for amyloid fibrils effect on living cells", Biosensors and Bioelectronics, vol. 52, pp. 89-97, Feb. 15, 2014.

Giaever et al., "Monitoring fibroblast behavior in tissue culture with an applied electric field", Proc. Natl. Acad. Sci. USA, vol. 81, pp. 3761-3764, Jun. 1984.

Kintzios et al., "Bioelectric recognition assay (BERA)", Biosensors & Bioelectronics, vol. 16, pp. 325-336, Jul. 2001.

Liu et al., "Detection of heavy metal toxicity using cardiac cell-based biosensor", Biosensors and Bioelectronics, vol. 22, Issue 12, pp. 3224-3229, Jun. 15, 2007.

Rider et al., "A B Cell-Based Sensor for Rapid Identification of Pathogens", www.sciencemag.org, Science, vol. 301, Issue 5630, pp. 213-215, Jul. 11, 2003.

Tarantola et al., "Cytotoxicity of Metal and Semiconductor Nanoparticles Indicated by Cellular Micromotility", ACS Nano, vol. 3, No. 1, pp. 213-222, published online Dec. 18, 2008.

Gheorghiu, U.S. Appl. No. 16/440,789, filed Jun. 13, 2019.

USPTO, Office Action dated Oct. 6, 2022 for U.S. Appl. No. 16/440,789, filed Jun. 13, 2019.

Bennet et al., "Light-Induced Anatomical Alterations in Retinal Cells," Analytical Biochemistry 436:84-92, May 2013.

Bennet et al., "Impedance-Based Cell Culture Platform to Assess Light-Induced Stress Changes with Antagonist Drugs Using Retinal Cells," Analytical Chemistry 85(10): 4902-4911, Apr. 2013.

* cited by examiner

SYSTEMS AND METHODS FOR MEASURING CELLULAR RESPONSE TO TARGET ANALYTES BY CONTROLLED APPLICATION OF AN OSCILLATING STIMULUS

CROSS-REFERENCE TO RELATED APPLICATIONS

This application claims priority to Romanian patent application Ser. A/00422/2018, by E. Gheorghiu et al., filed on Jun. 13, 2018, and to Romanian patent application Ser. A/00421/2018, by E. Gheorghiu et al., filed Jun. 13, 2018, which are incorporated herein by reference.

BACKGROUND

The invention relates to biosensing and immunoassay systems and methods.

Methods of detecting the presence of an analyte in solution, as well as of determining a response of living cells to an exposure to such analytes using principles of receptor-ligand interactions have been receiving attention worldwide. Such methods may have the sensitivities and specificities required by applications in medicine, as well as in the food and pharmaceutical industries. Target analytes of particular interest comprise biological cells such as bacteria, and also analytes of comparatively lower molecular weight such as and viruses, toxins, drugs, and DNA fragments.

A substantial limitation of conventional analytic methods resides in their limited sensitivity. Such methods detect changes in the electrochemical impedance or refractive index in the vicinity of a sensor, changes brought about by the presence of the analyte. Such differences are typically very small.

U.S. Pat. No. 9,315,855 B2 shows an example of using an oscillating physical stimulus (e.g., magnetic field) to enhance conventional impedance measurements and improve signal-to-noise ratio. There is continuing interest in developing methods and systems that facilitate sensitive measurements for biosensing and immunoassay applications.

SUMMARY

According to one aspect, the present invention comprises a method of processing measurements of an electrical impedance of an electrode pair contained within a measurement chamber, the electrode pair in contact with a liquid sample comprising a suspension of biological cells and magnetic beads functionalized to attach to the biological cells. The method comprises determining a plurality of reference impedance response values, wherein determining the plurality of reference impedance values comprises, for each frequency of a plurality of actuating frequencies, employing a magnet to apply an actuating magnetic field to the measurement chamber, the actuating magnetic field oscillating at the each actuating frequency, and determining a distinct member of the first plurality of reference impedance response values while the actuating magnetic field oscillates with the each actuating frequency. The method further comprises, in response to determining the first plurality of reference impedance response values, determining an optimal actuating frequency according to the plurality of reference impedance response values, and in response, employing the magnet to oscillate the actuating magnetic field at the optimal actuating frequency. The method further comprises determining a first impedance response value, and in response to a target analyte being introduced into the measurement chamber, determining a second impedance response value, both the first and second impedance response values determined while the actuating magnetic field oscillates at the optimal actuating frequency. The method further comprises determining a magnitude of a response of the biological cells to exposure to the target analyte according to the first and second impedance response values. All impedance response values characterize a response of the electrical impedance of electrode pair the to the actuating magnetic field.

According to another aspect, a system comprises an electrode pair contained within a measurement chamber, the electrode pair in contact with a liquid sample comprising a suspension of biological cells and magnetic beads functionalized to attach to the biological cells. The system further includes a sample actuator comprising a magnet configured to apply an oscillating magnetic field to the measurement chamber. The system further comprises a computer system connected to the sample actuator and to an electrical impedance analyzer configured to measure an electrical impedance of the electrode pair. The computer system includes at least one hardware processor configured to determine a plurality of reference impedance response values, wherein determining the plurality of reference impedance values comprises, for each frequency of a plurality of actuating frequencies, actuating the magnet to apply an actuating magnetic field to the measurement chamber, the actuating magnetic field oscillating at the each actuating frequency, and determining a distinct member of the first plurality of reference impedance response values while the actuating magnetic field oscillates with the each actuating frequency. The at least one hardware processor is further configured, in response to determining the first plurality of reference impedance response values, to determine an optimal actuating frequency according to the plurality of reference impedance response values, and. in response, to actuate the magnet to oscillate the actuating magnetic field at the optimal actuating frequency. The at least one hardware processor is further configured to determine a first impedance response value, and in response to a target analyte being added into the measurement chamber, determine a second impedance response value, both the first and second impedance response values determined while the actuating magnetic field oscillates at the optimal actuating frequency. The at least one hardware processor is further configured to determine a magnitude of a response of the biological cells to exposure to the target analyte according to the first and second impedance response values. All impedance response values characterize a response of the electrical impedance of electrode pair the to the actuating magnetic field.

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself.

The following description illustrates embodiments of the invention by way of example and not necessarily by way of limitation.

Figure 1:
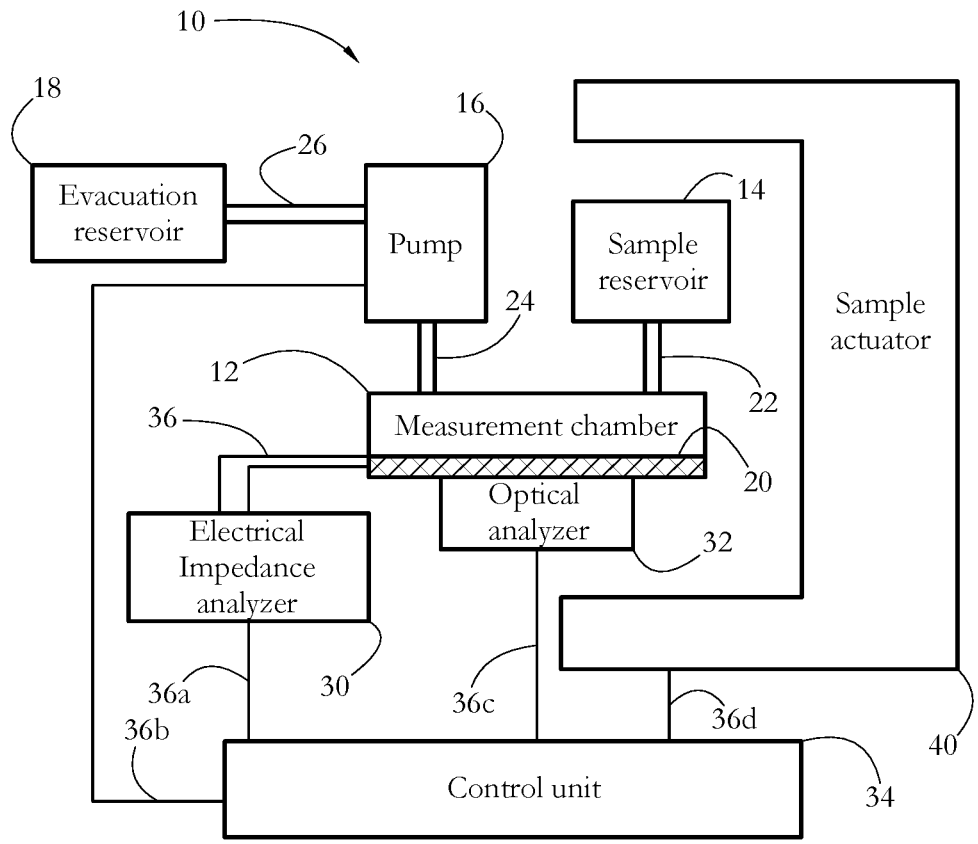
FIG. 1 shows a diagram of an exemplary measurement setup according to some embodiments of the present invention.

FIG. 1 shows a diagram of an exemplary system for measuring cellular response to a target analyte according to some embodiments of the present invention. System 10 comprises a measurement chamber 12 connected to a pump 16 through an evacuation tube 24, and to a sample reservoir 14 through an intake tube 22. Pump 16 is further connected to an evacuation reservoir 18. Measurement chamber 12 further includes a sensor 20 connected to an Electrical Impedance (EI) analyzer 30 and/or an optical analyzer 32.

In some embodiments, measurement chamber 12 is a sealed cavity, for instance of prismatic shape, having sensor 20 as a base and two openings at opposite ends, receiving tubes 22 and 24. In an exemplary configuration, tubes 22 and 24 are made of Teflon® and have an internal diameter of 0.5 mm. An exemplary pump 16 comprises a 2 ml syringe, and ensures a flow rate ranging from 0.00625 to 50.0 ml/min. An exemplary measurement chamber further comprises a silicone rubber seal, e.g. 100 μm in thickness, placed on the surface of the sensor. The seal may be pressed onto a biochemically-inert plastic (e.g. polyether-ether-ketone) wall to form a cavity comprising the actual fluid measurement area.

Chamber 12 is configured to receive a sample comprising a suspension of biological cells (e.g., bacteria, yeasts, animal tissue cells) and a chemical stimulating agent. At least a part of the sample biological cells may be alive. Exemplary stimulating agents include various chemical substances e.g., antibiotics, toxins, polypeptides, hormones, pesticides, drugs (e.g., chemotherapy pharmaceuticals), drug residues, etc., susceptible of inducing changes in some vital parameter of the living cells. For instance, chemical stimuli may induce changes in the properties of the cellular membrane, or even the death of the target cell. Such changes may be indirectly detected by measuring changes in some physical property (e.g., impedance, index of refraction) of the cell suspension, as shown in more detail below. Although the current disclosure will focus on an exemplary embodiment which monitors the response of living cells to a target analyte, a skilled artisan will appreciate that the systems and methods described herein can be applied to other biosensing applications, wherein living cells may be replaced, for instance, with cell fragments, organelles, viruses, DNA fragments, etc.

In some embodiments, the sample further comprises a suspension of magnetic indicator particles such as superparamagnetic microbeads, which may be chemically modified to attach to the sample cells, forming conglomerates herein deemed cell-bead clusters. In some embodiments, the application of an oscillating magnetic field within the measurement chamber determines oscillations in the position and/or shape of cell-bead clusters within the sample. The amplitude of such oscillations may be related to the magnetic properties and/or to the size of the respective conglomerates. Such oscillations may determine a variation in physical properties of the sample, which may be picked up by electrical and/or optical measurements as shown below.

In some embodiments, system 10 further comprises a sample actuator 40 configured to apply a variable magnetic field inside measurement chamber 12, as shown below. Pump 16, EI analyzer 30, optical analyzer 32, and sample actuator 40 are connected to a control unit 34 via communication lines 36a-d. In some embodiments, control unit 34 may be a computer system configured to control the operation of items 16 and 40, to receive data from EI analyzer 30 and optical analyzer 32, and to quantify a response of sample contained in measurement chamber 12 to exposure to a chemical stimulant/target analyte Control unit 34 comprises a processor (e.g. a microprocessor, a multi-core integrated circuit formed on a semiconductor substrate, etc.) configured to execute computational and/or logical operations with a set of signals and/or data, such as data provided by EI analyzer 30 and/or optical analyzer 32. In some embodiments, such operations are encoded in the form of a sequence of processor instructions, e.g., machine code. Control unit 34 further comprises volatile computer-readable media (e.g. DRAM, SRAM) storing instructions and/or data accessed or generated by the processor.

Figure 2:
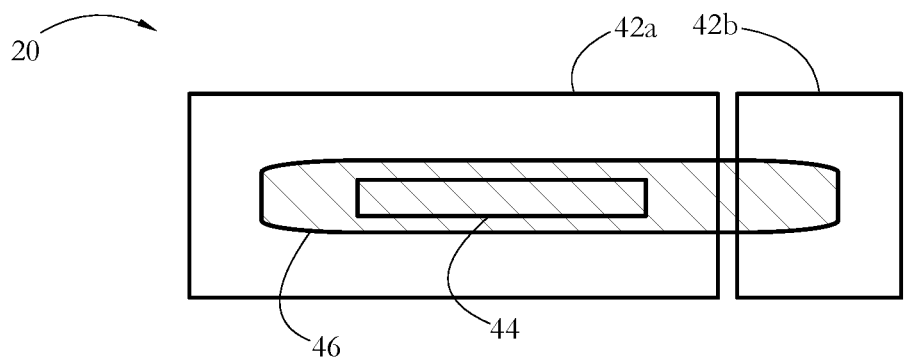
FIG. 2 shows a top view of an exemplary sensor forming part of the measurement chamber of FIG. 1, according to some embodiments of the present invention.

FIG. 2 shows a diagram of an exemplary sensor according to some embodiments of the present invention. In some embodiments, sensor 20 allows a determination of a variation of a property such as impedance and/or refractive index of the sensor surface, variation induced by the presence of a target analyte within the measurement chamber. Sensor 20 comprises a glass substrate covered in a metallic film patterned to form an electrode pair 42a-b, comprising an upper electrode 42a and a lower electrode 42b. In some embodiments, the glass substrate further comprises an optical measurement area 44 acting as a window for optical analyzer 32, and a fluid measurement area 46. Sensor 20 may be passivated by application of a thin layer of inert material. In some embodiments, passivation comprises applying a treatment to sensor 20, such as a chemical substance, which prevents sample constituents from attaching to the surface of sensor 20. In some embodiments, passivation may prevent a whole class of analytes and/or indicator particles from attaching to the sensor, so that the same sensor may be re-used for detecting a variety of analytes. In some embodiments, optical measurement area 44 and upper electrode 42a have substantial overlap. Having both optical and EI probes within a common fluid measurement area 46 yields potential advantages, such as the ability to continuously monitor the quality of the sensor surface and other parameters of the measurement chamber via optical measurements occurring simultaneously with electrical impedance measurements. An exemplary sensor 20 comprises a 0.3 mm thick glass slab, covered with a 50 nm gold layer patterned to produce electrode pair 42a-b, and passivated by e.g. coating with a self-assembled layer of thiols. An exemplary passivation method comprising immersing the sensor surface for 48 hours in a solution of 11-mercapto-undecanol.

Figure 3:
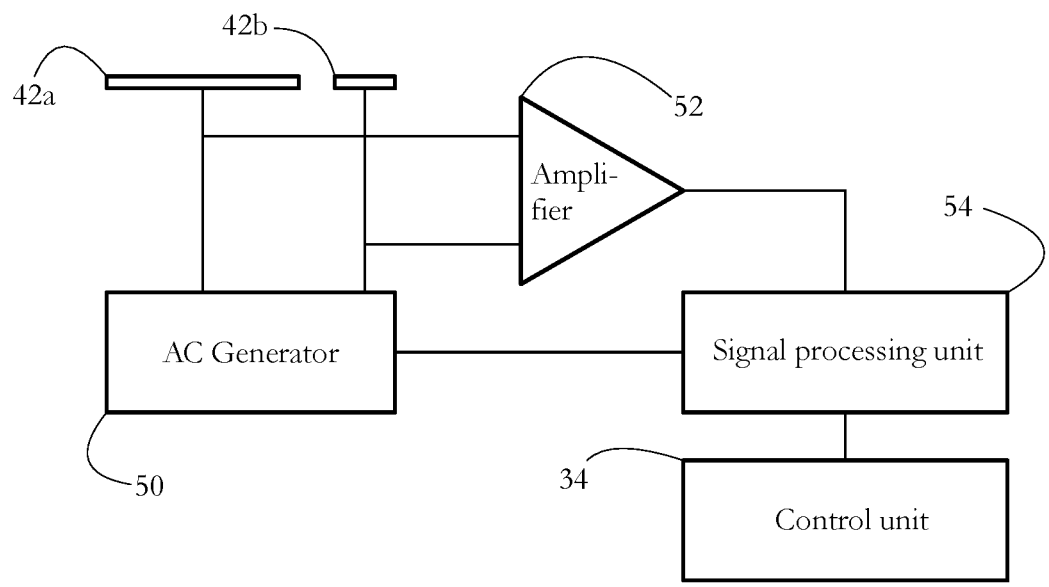
FIG. 3 illustrates an exemplary electrochemical impedance unit according to some embodiments of the present invention.

FIG. 3 shows a diagram of an exemplary EI analyzer 30 according to some embodiments of the present invention. EI analyzer includes an alternating current (AC) generator 50 configured to produce an oscillating electrical signal, an amplifier 52 configured to amplify and/or filter the electrical signal produced by generator 50, and a signal processing unit 54. In some embodiments, AC generator 50 produces a high frequency sinusoidal voltage with a range of amplitudes, e.g., 20 µV-2 mV, and a range of measurement frequencies such as 50 kHz or 500 kHz, which is applied to electrodes 42a-b of sensor 20. Changes in the impedance of electrodes 42a-b, caused by the application of an oscillating magnetic field as shown below, produce a signal which may be measured continuously between electrodes 42a-b. The signal is amplified and/or filtered by amplifier 52 and fed into signal processing unit 54. In some embodiments, signal processing unit 54 is configured to receive a signal from amplifier 52, convert the signal into a digital form, and transmit the digital form to control unit 34, e.g. through a serial communication interface.

Figure 4:
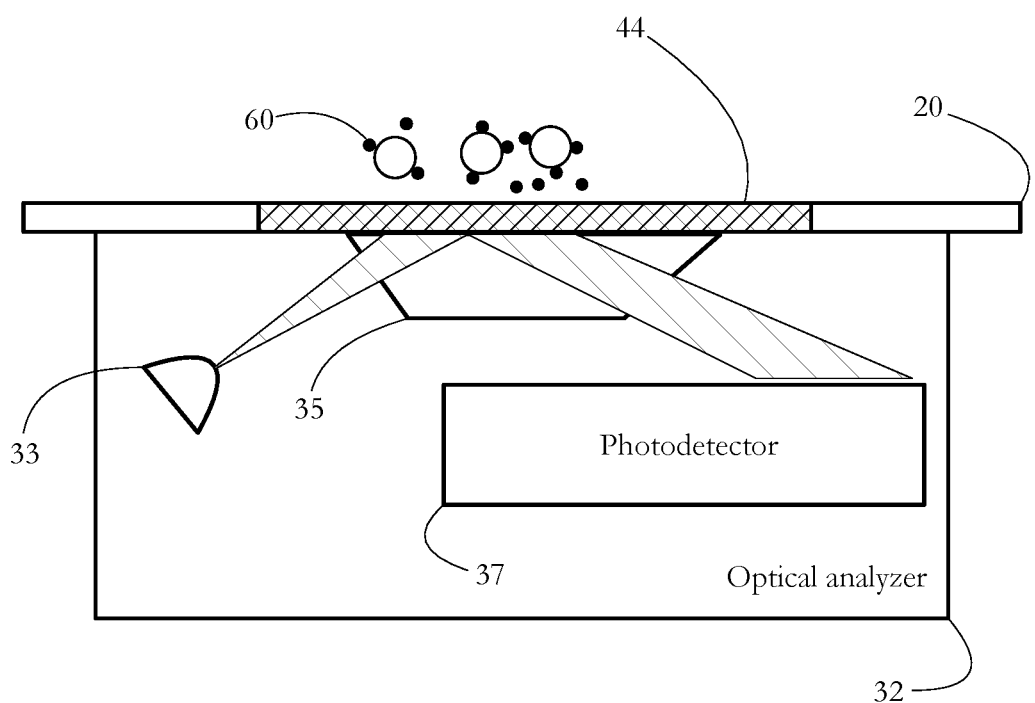
FIG. 4 shows a diagram of an exemplary optical analyzer according to some embodiments of the present invention.

FIG. 4 shows a diagram of an exemplary optical analyzer. In some embodiments, optical analyzer 32 is a Surface Plasmon Resonance (SPR) optical analyzer, comprising a polarized light source 33 such as an LED array, a transparent prism 35, and a photodetector 37. Optical analyzer 32 is configured to determine a value of the refractive index of a thin layer of sample in contact with optical measurement area 44 of sensor 20. In some embodiments, optical analyzer 32 is structured according to a Kretschmann prism configuration, wherein the surface of sensor 20 is illuminated by light source 33 at a plurality of predetermined incidence angles, and the intensity of the reflected light is measured by of photodetector 37. The incidence angle producing a resonant coupling between the incident light and the surface plasmons of the metallic film covering optical measurement area 44 is known as the SPR angle, and corresponds to a minimum in the intensity of the reflected light. The SPR angle is indicative of the optical properties, such as the refractive index, of a thin layer of sample in contact to the sensor surface. In some embodiments, the SPR angle is recorded, converted into digital form and transmitted to control unit 34. An exemplary optical analyzer 32 comprises a TSPR1K23 device from Texas Instruments, wherein sensor 20 sits on top of prism 35, and wherein the optical contact between prism 35 and sensor 20 is achieved through a thin layer of oil with an index of refraction chosen so as to minimize the deviation of the incident light.

Sample actuator 40 comprises a device configured to apply a variable physical stimulus to the sample inside measurement chamber 12, the physical stimulus producing a measurable variation of a physical property, such as a motion, or a change in shape, or a fluorescence, of a constituent of the sample. Physical stimuli may be magnetic, optical, electrical, or mechanical, among others. For simplicity, the following discussion will focus on a sample actuator 40 configured to deliver a low-frequency (e.g., 0.1-10 Hz) oscillating magnetic field to measurement chamber. In some embodiments, such an oscillating magnetic field may produce a displacement an/or a change of shape of an indicator particle and/or of a cell-bead conglomerate. These changes translate into changes in the physical properties (e.g., equivalent capacitance) of the sample. Properties of the oscillating magnetic field, such as intensity, time profile, and frequency of oscillation, may be adjustable by a user.

An exemplary embodiment of actuator 40 comprises two magnets: a superior magnet placed substantially above measurement chamber 12, and an inferior magnet placed substantially below chamber 12. The two magnets may include permanent magnets, e.g., NdFeB alloy cubes measuring 5 mm in size, having a remanent magnetic induction of 1 T. Each magnet may be connected to a stepper motor by a rod transforming rotational motion into linear motion. A magnet may thus be moved in an oscillatory fashion, the motion controlled by control unit 34. In an exemplary embodiment, the inferior magnet may produce a constant magnetic field with a gradient substantially perpendicular to sensor 20. A periodic displacement of the superior magnet along a direction substantially perpendicular to sensor 20 produces a magnetic field with a gradient variable in time. The frequency and time-profile of the intensity of the gradient may be chosen by a user according to particularities of the sample.

Figure 5:
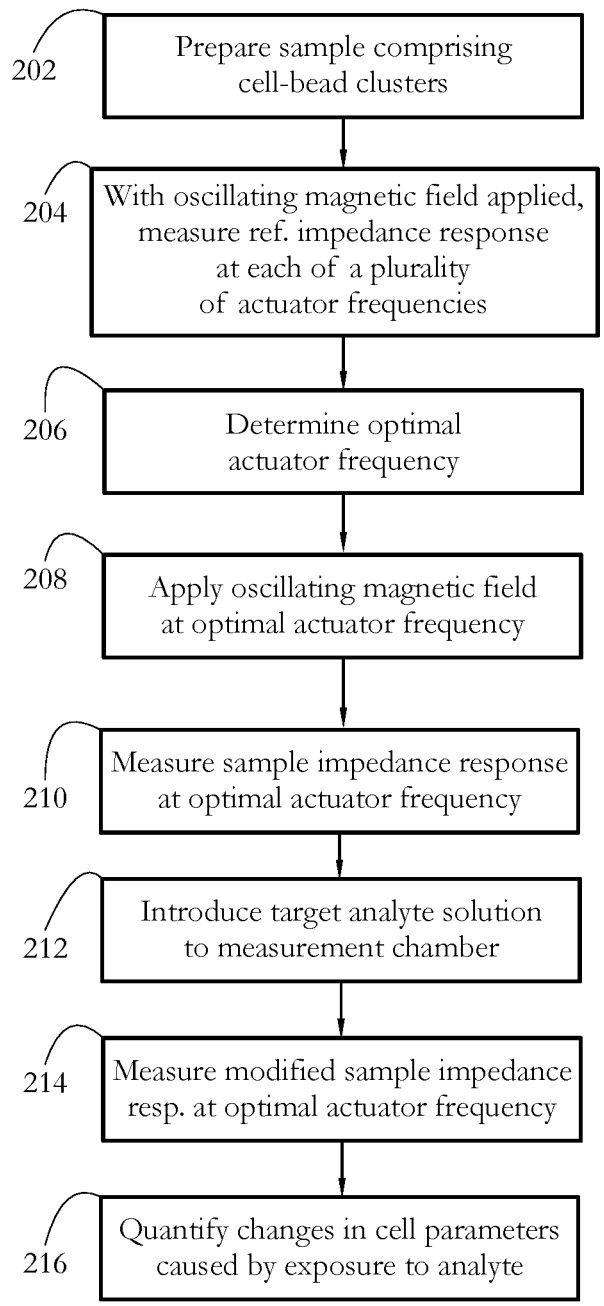
FIG. 5 shows an exemplary sequence of steps performed to measure cellular response to a target analyte according to some embodiments of the present invention.

FIG. 5 shows an exemplary sequence of steps performed to detect and quantify a cellular response to a target analyte according to some embodiments of the present invention. In some embodiments, the method includes binding magnetic indicator particles to the surface of living cells, and measuring changes in the electrical and/or optical properties of the sensor surface, changes determined by exposure of the resulting cell-bead clusters to a target analyte. Measurements are carried out in a low-frequency oscillating magnetic field supplied by sample actuator 40; such sample actuation is used to substantially improve the accuracy of measurements by boosting signal-to-noise ratio.

A step 202 comprises preparing a sample including a suspension of cell-bead clusters. In some embodiments, indicator particles such as super-paramagnetic microscopic beads (e.g. 500 nm Masterbeads® from Ademtech, Inc.) are functionalized by immobilizing affine compounds (e.g. antibodies, aptamers, etc.) on their surface, the affine compounds chosen to determine a specific binding of the respective indicator particles to target biological cells. Step 202 further includes incubating the functionalized indicator beads with selected biological cells (e.g., bacteria). Incubating fosters attachment of indicator beads to the cells, forming cell-bead clusters.

Figure 6:
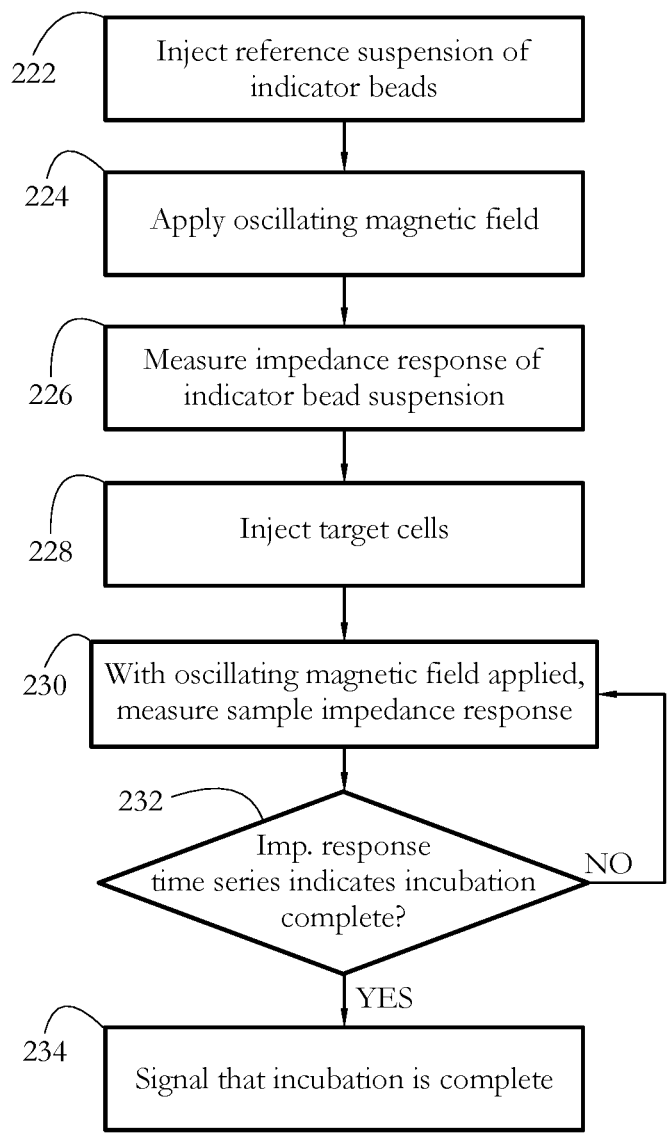
FIG. 6 illustrates an exemplary method for optimally incubating a sample comprising cell-indicator bead clusters, according to some embodiments of the present invention.
Figure 7:
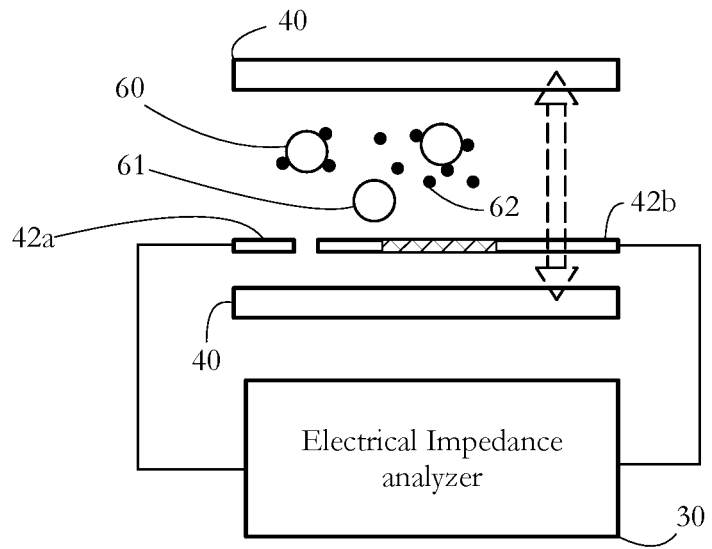
FIG. 7 shows a diagram of an incubation process for cell-bead clusters according to some embodiments of the present invention.

FIG. 6 shows an exemplary method of incubation according to some embodiments of the present invention. The illustrated method relies on repeated measurements of electrical impedance of the incubating sample, to determine a time-variation of the concentration of cell-bead clusters. FIG. 7 shows an exemplary setup for measuring impedance of the sample comprising a set of indicator beads 62, individual biological cells 61, and cell-bead clusters 60. In some embodiments, sample actuator 40 applies an oscillating low frequency magnetic field to the measurement chamber, and impedance measurements are performed while the actuating magnetic field is turned on.

Some embodiments further employ EI analyzer 30 to determine an impedance response of the sample to the oscillating actuation magnetic field. The impedance response quantifies changes in the sample impedance caused by application of the actuation field, and may be calculated according to an amplitude and/or a phase of oscillations in the actual impedance of the sample (i.e., measured impedance of electrode pair 42a-b). An exemplary impedance response is calculated as the modulus of the Fourier component of the measured impedance, the Fourier component corresponding to the frequency of the actuating magnetic field.

A step 226 calculates a baseline, reference impedance response corresponding to a zero concentration of cell-bead clusters. The baseline impedance response determination may be performed on a sample comprising only indicator beads, or alternatively, immediately following injection of the target biological cells (step 228). Instead of a single impedance response corresponding to a selected actuating frequency, some embodiments determine a plurality of such reference impedance responses, each response determined at a distinct actuating frequency.

Figure 8:
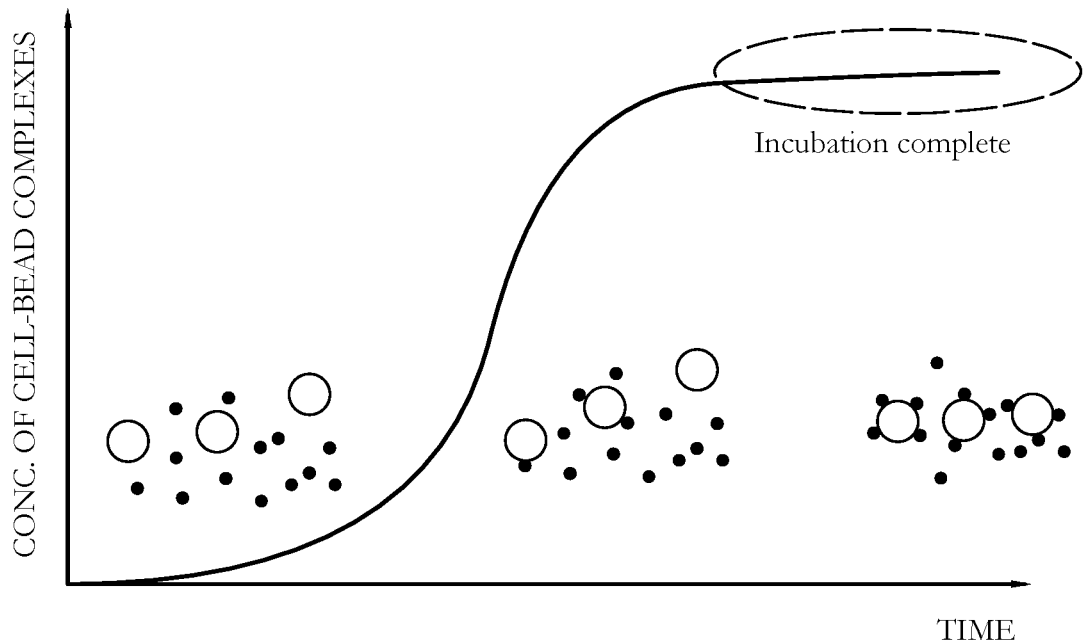
FIG. 8 illustrates an exemplary measurement of the electrical impedance of a sample comprising a suspension of cells, indicator beads, and cell-bead clusters according to some embodiments of the present invention.

Following cell injection, in a step 230, a time series of impedance responses is acquired to monitor the time evolution of incubation. An exemplary evolution of the concentration of cell-bead clusters in time is illustrated in FIG. 8. As time goes by, indicator beads are increasingly attaching to the cells, until a saturation regime is reached wherein the concentration of cell-bead clusters becomes stable. Some embodiments rely on the assumption that the cell-bead concentration plateau corresponds to an optimal incubation level, and that reaching such a plateau signals that incubation has finished.

Figure 9:
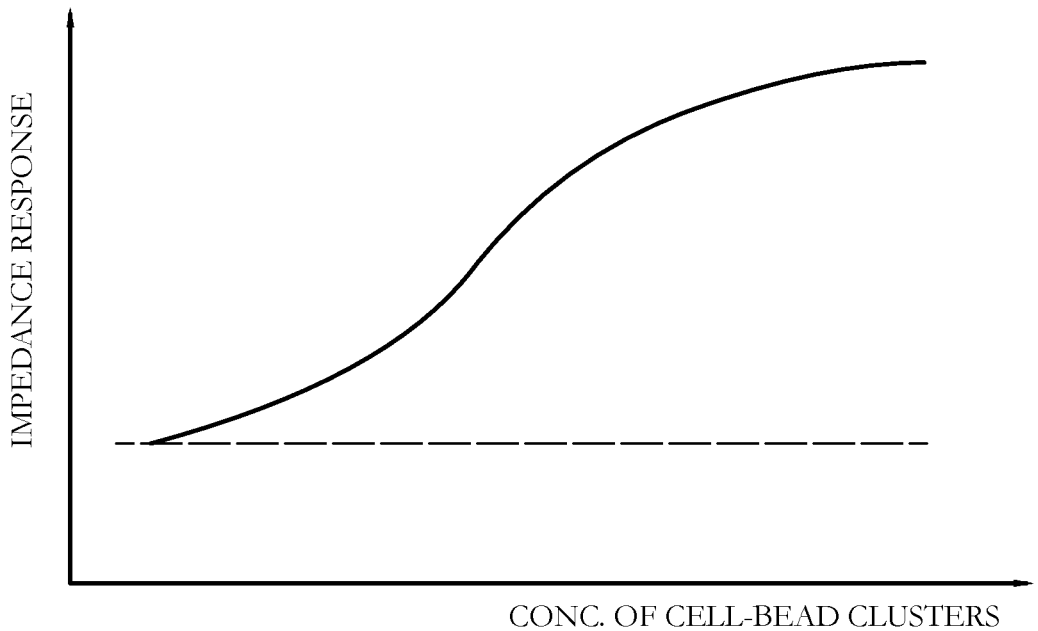
FIG. 9 shows an exemplary qualitative dependence of the impedance response on the concentration of cell-bead clusters, according to some embodiments of the present invention.

Since indicator beads are magnetic, cell-bead clusters are typically set in motion by the actuating magnetic field. As more and more cell-bead clusters are formed, progressively more such clusters are dragged into the vicinity of the impedance sensor, amplifying the impedance response of the sample. This physical effect allows some embodiments to accurately correlate the impedance response with the concentration of cell-bead clusters. An exemplary such correlation is illustrated in FIG. 9. Some embodiments of the present invention rely on the observation that the typical relation between the concentration of cell-bead clusters and impedance response is monotonic as in FIG. 9, and therefore an increase in the measured impedance response is likely indicative of an increase in the concentration of cell-bead clusters. Some embodiments therefore determine that an optimal level of incubation has been reached from the occurrence of a plateau in the time dependence of the measured impedance response of the sample. In FIG. 6, a step 232 may determine whether the impedance response time series verifies a plateau condition. For instance, step 232 may determine whether the average slope of the impedance response-vs.-time curve falls below a pre-determined threshold. When the impedance response verifies the plateau condition, some embodiments may signal to a human operator that incubation of the sample is complete (step 234). Otherwise, acquisition of the impedance response time series may continue (return to step 230).

Figure 10:
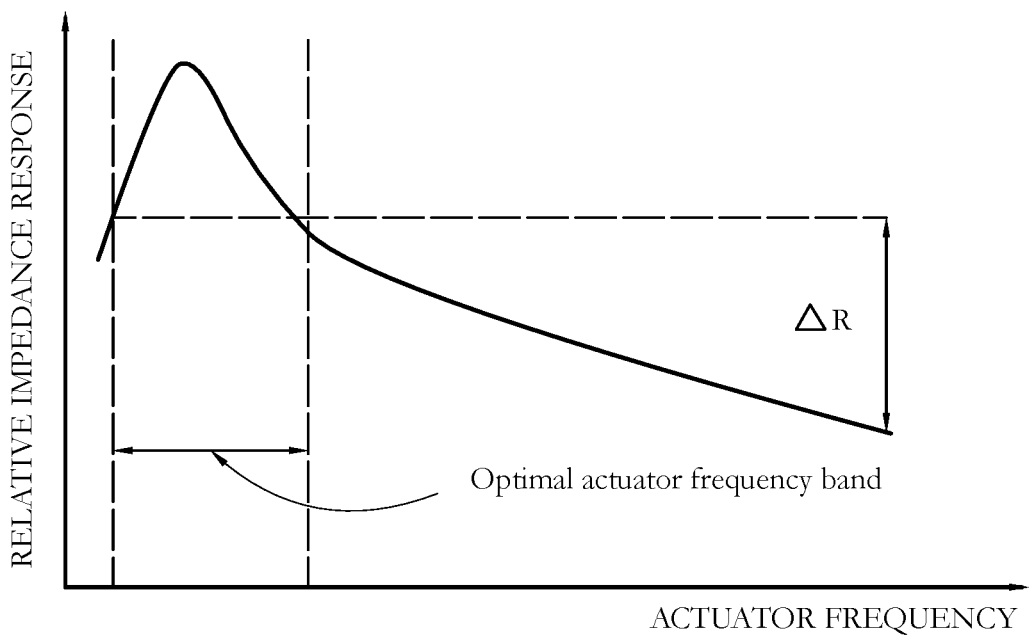
FIG. 10 shows an exemplary dependence of the impedance response of a sample on the frequency of the actuating oscillating magnetic field, and an optimal actuation frequency band according to some embodiments of the present invention.

Turning back to the method illustrated in FIG. 5, once incubation is complete, a step 204 performs a plurality of impedance response measurements of the incubated sample, each impedance response measured while the sample is subject to an oscillating magnetic field of a distinct frequency. For instance, for each of a plurality of actuating frequencies (typically in the range of 0.1 to 20 Hz), sample actuator 40 may apply an oscillating magnetic field with the respective frequency, and impedance analyzer 30 may record a set of impedance measurements. Then, an impedance response corresponding to the current actuating frequency may be calculated from the Fourier representation of the impedance time series. An exemplary dependence of the impedance response on actuating frequency according to some embodiments of the present invention is shown in FIG. 10. The illustrated curve plots impedance responses relative to (i.e., normalized by) reference impedance responses of a suspension comprising only beads, or of a non-incubated suspension of beads and cells. See e.g., description above related to step 226 in FIG. 6.

In a further step 206 (FIG. 5), an optimal actuating frequency is chosen according to impedance responses determined in step 204. Some embodiments rely on the observation that cell-bead clusters are set in motion by the actuating magnetic field, and the speed of the motion is controlled by the viscosity of the sample, size of the respective cell-bead cluster, and the count of beads actually attached to the respective cluster. A balance of forces applied to a simplified microscopic model of a cell-bead cluster reveals that:

$$v = v_b N_b \frac{r_b}{\left(N_b r_b^3 + N_{cel} r_{cel}^3\right)^{\frac{1}{3}}}, \quad [1]$$

wherein $v$ denotes the end velocity of a cell-bead cluster, $v_b$ denotes the end velocity of individual beads, $N_b$ the number of attached indicator beads, $r_b$ the bead radius, $N_{cel}$ the number of cells in the cell-bead cluster, and $r_{cel}$ the radius of individual cells. Cell-bead clusters containing more attached beads per cell move relatively faster that other cell-bead clusters of comparable size. Similarly, cell-bead clusters having fewer cells move relatively faster than other cell-bead clusters having approximately the same total count of attached beads. Moreover, in case of nonspecific bead-bead binding, bead-bead clusters will move relatively faster than cell-bead clusters. Some embodiments therefore explicitly tune the frequency of actuation (i.e., low frequency of oscillating magnetic field) to effectively separate bead-bead clusters from cell-bead clusters and/or to separate cell-bead clusters into classes according to their end-velocity. This effect may be used in various ways. For instance, such tuning of the actuation frequency may minimize the contribution to the impedance response from single beads and bead-bead clusters, and therefore amplify the useful signal from cell-bead clusters. In other embodiments, tuning of the actuation frequency may selectively boost the contribution of certain cell-bead clusters to the measured impedance response of the sample. In general, relatively higher actuating frequencies will enhance the relative contribution of more mobile clusters (e.g., clusters wherein multiple indicator beads attached to a single cell) to the overall impedance response. In turn, at relatively low actuating frequencies, all cell-bead clusters contribute to the measured impedance response. Some embodiments select an optimal actuation frequency according to the specific application. For instance, when the focus of the bio-assay is to quantify the response of individual cells to a target analyte, a relatively higher actuating frequency may be considered optimal. In contrast, when the focus is on clusters, a relatively lower actuating frequency may be selected. However, the particular value of such optimal frequencies depends explicitly on the nature of the sample (e.g., cell type, bead type, bead size, cell-bead affinity). Therefore, step 204 (FIG. 5) allows determining such properties by direct measurement.

Some embodiments focus on increasing the precision and accuracy of the measurement, and may therefore choose an optimal actuating frequency to maximize signal-to-noise ratio. Such embodiments may choose as optimal a value at or close to a maximum of the curve shown in FIG. 10. For instance, the frequency which gave the highest impedance response may be considered as optimal. An alternative embodiment may interpolate the calculated values of impedance response, and use a mathematical algorithm to determine the exact position of the maximum of the resulting smooth curve. Other exemplary embodiments may define an optimal actuation frequency band according to some performance criterion, e.g., an impedance response $\Delta R$ of at least 30% with respect to a non-actuated sample, and then choose at random an actuation frequency within the respective frequency band.

In response to choosing an optimal actuating frequency, in a step 208 the sample is actuated with an oscillating magnetic field of the optimal frequency. A further sequence of steps 210-212-214 determines the impedance response of the sample before and after introduction into the measurement chamber of the target analyte (e.g., toxin, antibiotic, pesticide, etc.). By comparing the modified impedance response to the one before injection of the target analyte, a further step 216 may quantify the response of the sample cells to the respective analyte.

In some embodiments, cell-bead complexes may be mathematically modelled using an equivalent resistor-capacitor (RC) electrical circuit. One way in which target analytes affect living cells is through changes in the physical properties of the cell membrane, and such changes are reflected into changes of the equivalent resistance and/or capacitance of the sample. Therefore, by measuring changes in the sample impedance caused by exposure to the target analyte, some embodiments may quantify relative changes in the cell membrane properties.

An exemplary application of the method illustrated in FIG. 5 determines the viability of living cells in response to exposure to target analytes such as antibiotics and chemotherapy agents, by indirectly monitoring the integrity of the cell membrane as revealed by changes in the impedance response between an initial state wherein the sample is free of the target analyte, and a final state wherein the sample contains the target analyte.

In an antibiotic assay example, the sample may contain living bacteria (e.g., *E. coli*), and the target analyte may comprise a bacteriostatic or bactericide substance. In a chemotherapy assay, the sample may contain living tumor cells, and the target analyte may comprise a cytotoxic substance. In some embodiments, the count/proportion of living and/or dead cells is derived from changes in the impedance response measured at two distinct measuring frequencies (i.e., high frequencies generated by the AC generator of the EI analyzer 30). The impedance response is typically higher for cell-bead complexes composed of living cells than for similar cell-bead complexes comprising dead cells. Therefore, monitoring the evolution of the impedance response of the sample in time allows an accurate estimation of the killing efficacy of the respective target analyte. For instance, at any time, the ratio of cells resistant to the action of the target analyte to those not resistant to the target analyte may be determined from the ratio between the impedance response at the current time and the reference impedance response measured in the absence of the target analyte.

In some embodiments, methods described in FIGS. 5-6 may be automated at least in part, i.e., may be executed by control unit 34 according to a computer program. Some method steps such as preparing the sample, injecting the target analyte, etc., may be executed by a human operator or may be automated, for instance by having control unit 34 actuate pump 16.

The exemplary systems and methods described above allow detecting and quantifying a cellular response to the exposure to a target analyte such as a toxin, drug, pesticide, etc. Some embodiments apply a variable physical stimulus (e.g., an oscillating magnetic field) to a sample containing an incubated suspension of target cells, magnetic beads, and cell-bead complexes. The physical stimulus produces changes in a physical, chemical or other property, such as a position, a shape, or a chemical structure, of a constituent of the sample, changes which may further determine measurable variations of a physical property, such as an impedance or an index of refraction, of a sensor surface. Such variations may be measured using e.g. electrical impedance or surface plasmon resonance analyzers.

In conventional measurements of impedance or refractive index, it may be difficult to detect small changes as are induced in a cellular membrane by the presence of a target analyte, because such small changes may be of the order of the measurement noise. In contrast to such conventional methods, some embodiments employ oscillating actuation of the sample to substantially improve signal-to-noise ratio, potentially by orders of magnitude.

Some embodiments of the present invention have other technical advantages as well. For instance, they allow expediting the incubation phase of an assay. Incubation of living cells with indicator bead particles to form cell-bead complexes is typically a long, laborious, and costly process. The progress of incubation and the quality of the incubated cell-bead complexes cannot be easily determined with conventional methods. Furthermore, a different incubation protocol may be established and tested every time sample ingredients such as target cells and indicator beads change. As shown herein, in contrast to such conventional incubation methods, some embodiments allow monitoring the impedance response of the sample to directly and quickly determine the progress of incubation, virtually irrespective of the sample composition.

A further technical advantage of some embodiments of the present invention is that instead of using an arbitrary frequency for the oscillating actuating magnetic field, they allow deliberately choosing an optimal frequency according to the specific application and/or sample composition. As shown herein, the actuating frequency may be tuned either to maximize the sensitivity of measurements (optimally enhance signal-to-noise ratio) or to selectively boost the contribution of certain sample components to the measured signal. For instance, in some samples, tuning the actuating frequency may allow predominantly detecting changes in single cells (as opposed to cell clusters) caused by exposure to the target analyte.

It will be clear to one skilled in the art that the above embodiments may be altered in many ways without departing from the scope of the invention. Accordingly, the scope of the invention should be determined by the following claims and their legal equivalents.

What is claimed is:

1. A method of processing measurements of an electrical impedance of an electrode pair contained within a measurement chamber, the electrode pair in contact with a liquid sample comprising a suspension of biological cells and magnetic beads functionalized to attach to the biological cells, the method comprising:
    determining a plurality of reference impedance response values, wherein determining the plurality of reference impedance values comprises, for each frequency of a plurality of actuating frequencies:
        employing a magnet to apply an actuating magnetic field to the measurement chamber, the actuating magnetic field oscillating at the each actuating frequency, and
        determining a distinct member of the first plurality of reference impedance response values while the actuating magnetic field oscillates with the each actuating frequency;
    in response to determining the first plurality of reference impedance response values, determining an optimal actuating frequency according to the plurality of reference impedance response values;
    in response to determining the optimal actuating frequency, employing the magnet to oscillate the actuating magnetic field at the optimal actuating frequency;
    determining a first impedance response value while the actuating magnetic field oscillates at the optimal actuating frequency;
    in response to determining the first impedance response value, and in response to a target analyte being introduced into the measurement chamber, determining a second impedance response value while the actuating magnetic field oscillates at the optimal actuating frequency; and
    determining a magnitude of a response of the biological cells to exposure to the target analyte according to the first and second impedance response values,
    wherein all impedance response values characterize a response of the electrical impedance of the electrode pair to the actuating magnetic field.

2. The method of claim 1, wherein the magnitude of the response of the biological cells is determined according to a proportion of the biological cells that are dead at the time of determination of the second impedance response value.

3. The method of claim 1, wherein the magnitude of the response of the biological cells is determined according to an equivalent capacitance of a region of the measurement chamber located in the vicinity of the electrode pair.

4. The method of claim 1, wherein the magnitude of the response of the biological cells characterizes a relative change of an average cellular membrane capacitance of the biological cells.

5. The method of claim 1, further comprising:
    in preparation for determining the plurality of reference impedance response values, determining a plurality of baseline impedance response values while the measurement chamber contains another suspension of magnetic beads, wherein determining the plurality of baseline impedance values comprises, for each frequency of the plurality of actuating frequencies:
        employing the magnet to oscillate the actuating magnetic field at the each actuating frequency, and
        determining a distinct member of the first plurality of baseline impedance response values while the actuating magnetic field oscillates with the each actuating frequency; and
    determining the optimal actuating frequency further according to the plurality of baseline impedance response values.

6. The method of claim 5, comprising determining the optimal actuating frequency according to a ratio between a reference value selected from the plurality of reference values and a baseline value selected from the plurality of baseline values, wherein the reference and baseline values are determined while the actuating magnetic field oscillates at the same actuating frequency.

7. The method of claim 1, wherein determining the optimal actuating frequency comprises comparing a first reference value selected from the plurality of reference impedance values to a second reference value selected from the plurality of reference impedance values, and determining the optimal actuating frequency according to a result of the comparison.

8. The method of claim 1, further comprising:
    in preparation for determining the first impedance response value, acquire a time series comprising a plurality of impedance response values determined at distinct moments in time;
    determine according to the time series an incubation progress indicator characterizing a proportion of magnetic beads that are bound to biological cells within the suspension; and
    determine whether to proceed with determining the first impedance response value according to the incubation progress indicator determined extent.

9. The method of claim 8, further comprising determining the incubation progress indicator according to a difference between two impedance response values of the time series.

10. A system comprising:
    an electrode pair contained within a measurement chamber, the electrode pair in contact with a liquid sample comprising a suspension of biological cells and magnetic beads functionalized to attach to the biological cells;
    a sample actuator comprising a magnet configured to apply an oscillating magnetic field to the measurement chamber; and
    a computer system connected to the sample actuator and to an electrical impedance analyzer configured to measure an electrical impedance of the electrode pair, the computer system comprising at least one hardware processor configured to:
        determine a plurality of reference impedance response values, wherein determining the plurality of reference impedance values comprises, for each frequency of a plurality of actuating frequencies:
            actuating the magnet to apply an actuating magnetic field to the measurement chamber, the actuating magnetic field oscillating at the each actuating frequency, and determining a distinct member of the first plurality of reference impedance response values while the actuating magnetic field oscillates with the each actuating frequency;

in response to determining the first plurality of reference impedance response values, determine an optimal actuating frequency according to the plurality of reference impedance response values;

in response to determining the optimal actuating frequency, actuate the magnet to oscillate the actuating magnetic field at the optimal actuating frequency;

determine a first impedance response value while the actuating magnetic field oscillates at the optimal actuating frequency;

in response to determining the first impedance response value, and in response to a target analyte being added into the measurement chamber, determine a second impedance response value while the actuating magnetic field oscillates at the optimal actuating frequency; and determine a magnitude of a response of the biological cells to exposure to the target analyte according to the first and second impedance response values, wherein all impedance response values characterize a response of the electrical impedance of the electrode pair to the actuating magnetic field.

11. The system of claim 10, wherein the magnitude of the response of the biological cells is determined according to a proportion of the biological cells that are dead at the time of determination of the second impedance response value.

12. The system of claim 10, wherein the magnitude of the response of the biological cells is determined according to an equivalent capacitance of a region of the measurement chamber located in the vicinity of the electrode pair.

13. The system of claim 10, wherein the magnitude of the response of the biological cells characterizes a relative change of an average cellular membrane capacitance of the biological cells.

14. The system of claim 10, wherein the at least one hardware processor is further configured to:

in preparation for determining the plurality of reference impedance response values, determine a plurality of baseline impedance response values while the measurement chamber contains another suspension of magnetic beads, wherein determining the plurality of baseline impedance values comprises, for each frequency of the plurality of actuating frequencies:

actuating the magnet to oscillate the actuating magnetic field at the each actuating frequency, and determining a distinct member of the first plurality of baseline impedance response values while the actuating magnetic field oscillates with the each actuating frequency; and determine the optimal actuating frequency further according to the plurality of baseline impedance response values.

15. The system of claim 14, wherein the at least one hardware processor is configured to determine the optimal actuating frequency according to a ratio between a reference value selected from the plurality of reference values and a baseline value selected from the plurality of baseline values, wherein the reference and baseline values are determined while the actuating magnetic field oscillates at the same actuating frequency.

16. The system of claim 10, wherein determining the optimal actuating frequency comprises comparing a first reference value selected from the plurality of reference impedance values to a second reference value selected from the plurality of reference impedance values, and determining the optimal actuating frequency according to a result of the comparison.

17. The system of claim 10, wherein the at least one hardware processor is further configured to:

in preparation for determining the first impedance response value, acquire a time series comprising a plurality of impedance response values determined at distinct moments in time;

determine according to the time series an incubation progress indicator characterizing a proportion of magnetic beads that are bound to biological cells within the suspension; and determine whether to proceed with determining the first impedance response value according to the incubation progress indicator determined extent.

18. The system of claim 17, wherein the at least one hardware processor is configured to determine the incubation progress indicator according to a difference between two impedance response values of the time series.

* * * * *